United States Patent [19]

Gradeff et al.

[11] Patent Number: 5,017,695

[45] Date of Patent: * May 21, 1991

[54] CERIC HYDROCARBYL SILYLOXIDES AND PROCESS FOR THEIR PREPARATION

[75] Inventors: Peter S. Gradeff, Pottersville; Kenan Yunlu, Highland Park, both of N.J.

[73] Assignee: Rhone-Poulenc, Inc., New Brunswick, N.J.

[ * ] Notice: The portion of the term of this patent subsequent to Sep. 21, 2006 has been disclaimed.

[21] Appl. No.: 128,245

[22] Filed: Dec. 3, 1987

[51] Int. Cl.$^5$ ................................................ C07F 5/00
[52] U.S. Cl. ..................................................... 534/15
[58] Field of Search ........................................... 534/15

[56] References Cited

U.S. PATENT DOCUMENTS

| | | | |
|---|---|---|---|
| 3,267,036 | 8/1964 | Baker et al. | 534/15 X |
| 3,884,950 | 5/1975 | Koda et al. | 252/49.7 X |
| 4,070,343 | 1/1978 | Kishimoto et al. | 252/49.7 X |
| 4,489,000 | 12/1985 | Gradeff et al. | 260/429.2 |
| 4,663,439 | 5/1987 | Gradeff et al. | 534/15 |

OTHER PUBLICATIONS

Brown, L. et al., "Synthesis and Some Properties of Yttrium and Lanthanide Isopropoxides", *Inorganic Chemisty*, vol. 9, No. 12 (1970), pp. 2783-2786.

Misra, S. et al., "Organic Compounds of Lanthanide Elements", *Aust. Journal of Chemistry*, vol. 21 (1968), pp. 797-800.

Mehrotra, R. et al., "Preparation of Some Reactions of Alkoxides of Gadolinium and Erbrium", *Inorganic Chemistry*, vol. 9, No. 11 (1970), pp. 2505-2509.

Tripathi, U. et al., "Alcoholates and Alkoxides of Ytterbium", *Journal of Chemical Science*, (A), (1967), pp. 991-992.

Bradley, D. et al., "Structural Chemistry of the Alkoxides, Part VI Primary Alkoxides of Quadravalent Cerium and Thorium", *J.C.S.* (1956), pp. 2260-2264.

Bradley, D. et al., "Organosilyloxy-Derivatives of Metals, Part I. Alkyl Silyloxy Derivatives of Titanium Zirconium, Niobium and Tantalum", *J. Chem. Society,* (1959), pp. 3404-3410.

Bradley, D. et al., "Metal Oxide Trialkylsilyoxide Polymers, Part II, Zirconium Oxide Trimethylsilyloxide Polymers", *J. Chem. Soc.*, (1964), pp. 1580-1584.

Rad'Kov, Y. et al., "Derivatives of Lanthanides", *J. of Gen. Chem. of the U.S.S.R.*, (1986), pp. 336-338.

Batwara, J. et al., "Synthesis of Silyloxides of Gadolinium and Erbium", *Journal of Inorganic Nuclear Chemistry*, vol. 32, (1970), pp. 411-415.

*Primary Examiner*—John S. Maples
*Assistant Examiner*—Cynthia Harris

[57] ABSTRACT

Ceric hydrocarbyl silyloxides are provided, as well as a process for preparing them, which comprises reacting ceric ammonium nitrate with a hydrocarbyl silanol, including a lower aliphatic silanol, under anhydrous conditions in the presence of an anhydrous base at a temperature within the range from about −30° C. to about 200° C. but preferably from 0° to about 150° C. until ceric hydrocarbyl silyloxide and the nitrate salt of the base are formed; the nitrates formed during the reaction can be separated from the reaction mixture and the ceric hydrocarbyl silyloxides isolated pure or as complexes with the solvent, or in some cases the ceric hydrocarbyl silyloxides can be used without separation from the reaction mixture in the presence of the nitrates.

17 Claims, No Drawings

CERIC HYDROCARBYL SILYLOXIDES AND PROCESS FOR THEIR PREPARATION

Polyvalent metal alkoxides are an important class of versatile organometallic compounds that have many industrial uses. In some instances their uses parallel the metal carboxylates and other organometallic compounds, but they have advantages over such compounds because of their catalytic properties, ease of hydrolysis, solubility in organic solvents, and volatility. They have been used as paint additives, water repellents, adhesion promoters, mordants, sizing agents in enamel compositions, catalysts and also very importantly as intermediates in synthesis of other organic compounds.

There are four general preparative methods for metal alkoxides, all under anhydrous conditions, as follows:

A. By reaction of the corresponding alcohol and metal, such as the alkali metals, alkaline earth metals, and aluminum, with the assistance of an alkaline or acidic catalyst.

B. By reaction of the corresponding alcohol with the oxides and hydroxides of the metal, for instance NaOH or $Na_2O$, $V_2O_5$ and $MoO_3.5H_2O$.

C. By reaction of the corresponding alcohol and metal halide in the presence of an anhydrous base. A typical example is the preparation of $Th(OR)_4$ or $Zr(OR)_4$:

The reaction can be used for preparing alkoxides of titanium, hafnium, germanium, niobium, tantalum, aluminum and tin.

D. By transetherification of the metal alkoxides of lower alcohols, such as the methoxides, ethoxides or isopropoxides, with a higher alcohol.

Method A is exemplified for a number of yttrium, lanthanum and other lanthanide alkoxides by L. Brown and K. Mazdiyasni in *Inorganic Chemistry*, (1970) 2783. The reaction, previously thought to be useful only for the alkali metals, magnesium and aluminum, was extended by them to the synthesis of yttrium and all of the lanthanide isopropoxides. For the lower lanthanides, such as lanthanum, cerium, praesodymium and neodymium, a mixture of $HgCl_2$ and $Hg(C_2H_3O_2)_2$ or $HgI_2$ is used as a catalyst, to increase both the rate of reaction and percent yield. Generally, 5 g of metal turnings is reacted with about 300 ml of isopropyl alcohol at reflux temperature for about 24 hours and in the presence of a small amount of Hg salt catalyst. The yields are said to be 75% or better.

Most of the other examples in the literature of the preparation of alkoxides of lanthanides refer to the use of the corresponding metal halides. In some cases, a complex $LaCl_3.3ROH$ is preferred to the $LaCl_3$ (Misra et al, *Austr. J. Chem.* 21 797 (1978) and Mehrotra and Batwara, *Inorganic Chem.* 9 2505 (1970)).

An interesting variation of Method D is mentioned by Tripathi, Batwara, and Mehrotra *J.C.S.A.* 1967 991. Lower ytterbium alkoxides (such as the methoxide and ethoxide) were synthesized from ytterbium isopropoxide, by transetherification with methanol or ethanol. Owing to their sparing solubility, these alcohols were removed by precipitation as the reaction proceeded, driving the transetherification to completion.

In general, Methods A, B and C are only suited for preparation of the lower alkoxides, such as the methoxides, ethoxides and isopropoxides, since the reactivity of higher alcohols diminishes with increase in their molecular weights. The higher alkoxides are better prepared by Method D, which is a two-step process.

The only published method for preparing ceric alkoxides applied Method C to ceric chloride, Bradley et al, *J.C.S.* 1956 2260–64. Since cerium tetrachloride is unstable, the dipyridinium cerium hexachloride complex was Bradley et al's choice as starting material.

Cerium dioxide was first converted to ceric ammonium sulphate. Pure ceric hydroxide was precipitated from an aqueous solution of ceric ammonium sulphate and washed thoroughly. The freshly-prepared ceric hydroxide, suspended in absolute alcohol, was treated with anhydrous hydrogen chloride and then pyridine was added, which formed the insoluble dipyridinium cerium hexachloride complex $(Py)_2CeCl_6$. The complex was filtered, dried, and used for preparing the methoxide, ethoxide and isopropoxide directly, while the propyl, butyl, secondary butyl, neopentyl and n-pentyl alkoxides were made by alcohol interchange, i.e., transetherification, from the isopropoxide. The methoxide and ethoxide were also made by exchange from the isopropoxide.

Gradeff and Schreiber, U.S. Pat. Nos. 4,489,000, patented Dec. 18, 1984 and 4,663,439, patented May 5, 1987 provide a process for preparing ceric alkoxides which comprises reacting ceric ammonium nitrate with an alcohol under anhydrous conditions in the presence of an anhydrous base at a temperature within the range from about −30° C. to about 200° C., preferably from about 0° C. to about 150° C., until ceric alkoxide and the nitrate salt of the base are formed.

This process avoids the necessity described by Bradley et al of first preparing the ceric hydroxide from the ceric salt, in their case, ceric ammonium sulphate, and converting the hydroxide subsequently to the chloride, which needs to be stabilized as the pyridine complex.

It is rather surprising, despite the considerable volume of work done on the preparation of rare earth metal silicon compounds, that cerium hydrocarbyl silyloxides are unknown, as well as a suitable process for preparing them.

Bradley and Thomas, *J. Chem. Soc.* 1959 3404 have reported work on alkyl silyloxy derivatives of titanium, zirconium, neobium and tantalum, using trimethyl silanolysis of titanium or zirconium isopropoxides, or using trialkyl silyl acetate in place of the silanol, but there is no reference to cerium.

Bradley and Prevedorou-Demas, *J. Chem. Soc.* 1964 1580 reported further work on zirconium oxide trimethyl silyloxide polymers.

In neither paper is there reference to cerium silyloxides.

In accordance with the present invention, a process is provided for preparing ceric hydrocarbyl silyloxides which comprises reacting ceric ammonium nitrate with a silanol under anhydrous conditions in the presence of an anhydrous base at a temperature within the range from about −30° C. to about 200° C., preferably from about 0° C. to about 150° C., until ceric hydrocarbyl silyloxide and the nitrate salt of the base are formed.

This process is direct and economical, and in addition utilizes ceric ammonium nitrate, a commercially available material that is relatively inexpensive.

The product, a ceric hydrocarbyl silyloxide, is believed to be novel, since it has not previously been reported in the literature, and is characterized by one or more groups having a tetravalent cerium linked via oxygen to one, two, three or four silicon atoms, as shown, the remaining three or two, respectively, valences of the silicon being linked to hydrocarbyl groups having from one to about ten carbon atoms. The compounds can have one, two, three or four silicon atoms, in a single unit, or in a plurality of such units linked in linear, branched or cage-type oligomers or polymers, when the starting silanol is a diol.

In addition, if desired, a ceric hydrocarbyl silyloxide nitrate, is formed when the amount of silanol is less than the stoichiometric amount required to react with all of the valence positions of the cerium, and can be isolated from the reaction mixture. These free valence positions of the cerium thus carry $NO_3$ groups instead of silyloxide groups.

A ceric hydrocarbyloxy hydrocarbyl silyloxide can be formed by transetherifying a ceric hydrocarbyl oxide with silanol and by employing an amount of silanol that is less than the stoichiometric amount required to react with all of the valence positions of the cerium, so that only part of the hydrocarbyloxy groups are displaced by silyloxide groups. These valence positions of the cerium thus carry hydrocarbyloxy groups.

Accordingly, to prepare a ceric hydrocarbyloxy hydrocarbyl silyloxide, a ceric alkoxide is transetherified with the silanol having the desired hydrocarbyl group and the desired number of hydroxyl groups under anhydrous conditions at a temperature within the range from about $-30°$ C. to about $200°$ C., thereby displacing part of the aliphatic alcohol of the alkoxide and forming the ceric hydrocarbyloxy hydrocarbyl silyloxide of the silanol. The ceric hydrocarbyloxy hydrocarbyl silyloxide if insoluble in the reaction mixture precipitates out in the course of the transetherification.

Accordingly, the ceric hydrocarbyl silyloxides can be defined by the following general formula:

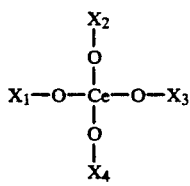

I where $OX_1$, $OX_2$, $OX_3$ and $OX_4$ are selected from the group consisting of $OR_1$, $NO_3$ and $[O]_{4-y}SiR_y$; and any two of $X_1$ and $X_2$ and $X_3$ and $X_4$ can be taken together as $>SiR_y$; the number of $SiR_y$ can be 1, 2, 3 or 4 and y can be 1, 2 or 3.

When $y=2$, the silicon is linked to two of the oxygens as $>SiR_y$ in (1) the same or (2) a different cerium atom; in (1) the species are monomeric; in (2) they can be oligomers or polymers.

At least one of $X_1$, $X_2$, $X_3$ and $X_4$ is $O_{4-y}SiR_y$, at least one R is hydrocarbyl, and no more than one R may be hydrogen.

Examples of compounds falling within Formula I according to the value of $X_1$, $X_2$, $X_3$, $X_4$ include:

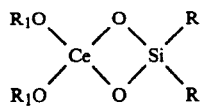 1.

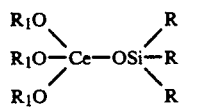 2.

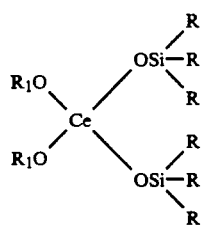 3.

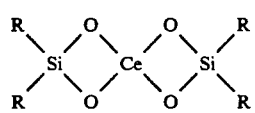 4.

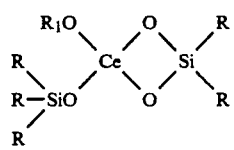 5.

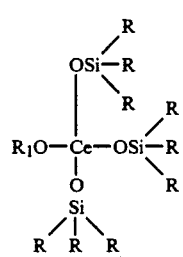 6.

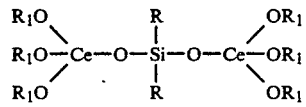 7.

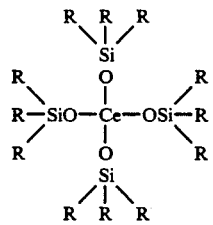 8.

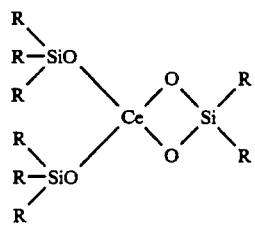 9.

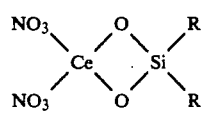 10.

-continued

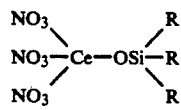

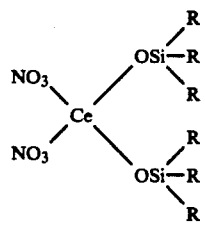

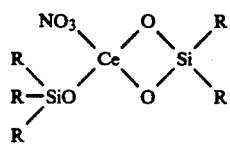

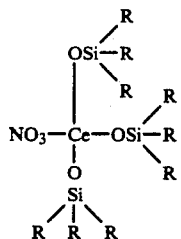

15.
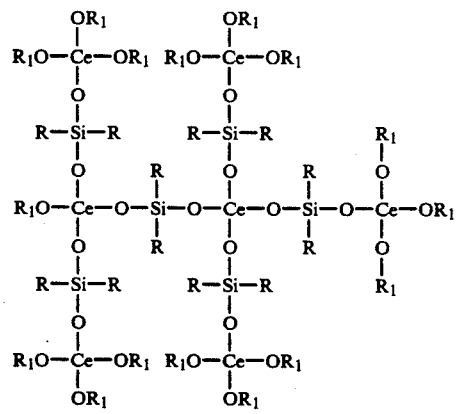

16.
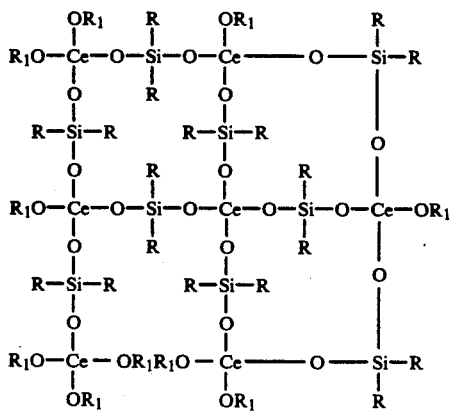

-continued

17.
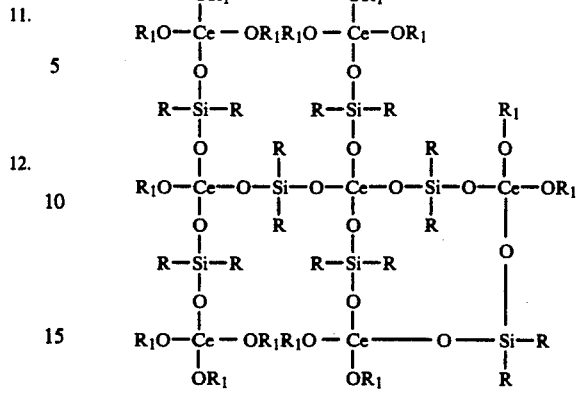

18.
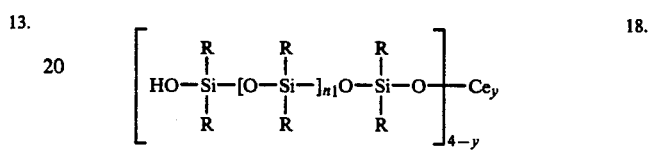

wherein y is the number of cerium atoms in the polymer and can range from 1 to about 10.

19.
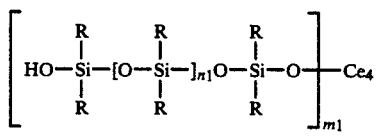

wherein $m_1$ is the number of such units in the polymer and can range from 1 to about 10.

R in the above formulae is hydrogen or a hydrocarbyl group having from one to about ten carbon atoms, and the R's attached to any silicon can be the same or different.

$R_1$ is a hydrocarbyl group attached via oxygen to cerium and having from one to about ten carbon atoms, and the $R_1$'s attached to any cerium can be the same or different.

Exemplary hydrocarbyl R and $R_1$ groups include alkyl, straight or branched alkenyl, cycloalkyl, cycloalkenyl, phenyl and alkyl phenyl, naphthyl and alkyl naphthyl groups.

Exemplary R and $R_1$ alkyl include methyl, ethyl, propyl, isopropyl, butyl, sec-butyl, hexyl, octyl, isooctyl, 2-ethylhexyl, nonyl and decyl.

Exemplary R and $R_1$ alkenyl include vinyl, allyl, butenyl, hexenyl, octenyl, nonenyl and decenyl.

Exemplary R and $R_1$ cycloalkyl include cyclopentyl, cyclohexyl, cycloheptyl and cyclooctyl; cyclopentenyl, cyclohexenyl and cycloheptenyl.

Exemplary R and $R_1$ alkaryl include phenyl, phenylmethyl, and phenylethyl.

The hydrocarbyl silanol can be any of several types:

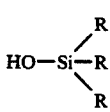 (a)

-continued

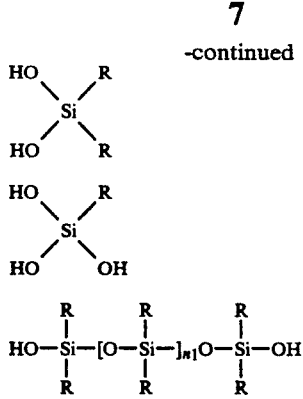

wherein $n_1$ is the number of such units in the polymer and can range from 1 to about 10.

Group (d) includes solid silicone resins containing free OH groups, which can be solubilized and used in the reaction with ceric ammonium nitrate to form silicone resin linked to cerium via the oxygen.

R is hydrogen or the hydrocarbyl group desired in the silyloxide product, and the R's attached to any silicon can be the same or different.

Preferred subclasses of silanols include:

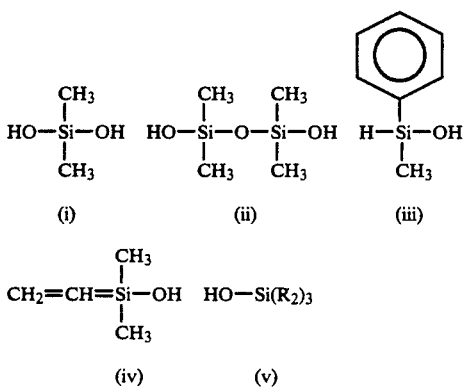

$R_2$ = methyl, ethyl, phenyl

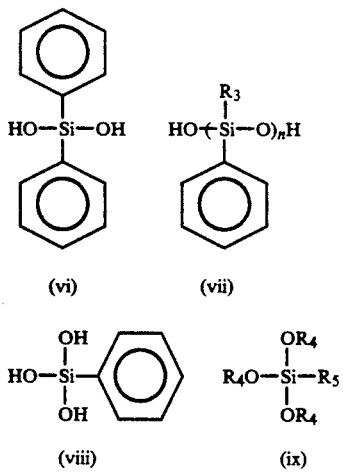

n = 4
$R_3$ = hydrocarbyl of 1 to 6 carbons
$R_4$ = methyl, ethyl, propyl, butyl, isopropyl
$R_5$ = methyl, ethyl, vinyl, phenyl The process proceeds with ease with the lower aliphatic monohydric, dihydric and trihydric silanols having one, two or three hydrocarbyl groups of from one to six carbon atoms, for example, trimethyl silanol, triethyl silanol, tripropyl silanol, triisopropyl silanol, tributyl silanol, triisobutyl silanol, tri-sec-butyl silanol, tri-tert-butyl silanol, tripentyl silanol, triisopentyl silanol, tri-sec-pentyl silanol, tri-tert-pentyl silanol, and trihexyl silanol; dimethyl silanediol, diethyl silanediol, dipropyl silanediol, diisopropyl silanediol, dibutyl silanediol, diisobutyl silanediol, di-sec-butyl silanediol, di-tert-butyl silanediol, dipentyl silanediol, diisopentyl silanediol, di-sec-pentyl silanediol, di-tert-pentyl silanediol and dihexyl silanediol; methyl silanetriol, ethyl silanetriol, propyl silanetriol, isopropyl silanetriol, butyl silanetriol, isobutyl silanetriol, sec-butyl silanetriol, tert-butyl silanetriol, pentyl silanetriol, isopentyl silanetriol, sec-pentyl silanetriol, tert-pentyl silanetriol and hexyl silanetriol.

A higher aliphatic, cycloaliphatic or aromatic hydrocarbyl silanol having hydrocarbyl groups of at least seven up to about ten carbon atoms can be incorporated directly in the reaction mixture together with a lower aliphatic silanol having hydrocarbyl groups of from one to six carbon atoms to form a ceric silyloxide of the higher silanol. Exemplary are triheptyl silanol, triisoheptyl silanol, trioctyl silanol, triisooctyl silanol, tri-2-ethyl-hexyl silanol, tri-sec-octyl silanol, tri-tert-octyl silanol, trinonyl silanol, triisonoyl silanol, tridecyl silanol, tricyclopropyl silanol, tricyclobutyl silanol, tricyclopentyl silanol, tricyclohexyl silanol, tricycloheptyl silanol, tricyclooctyl silanol, tripropyl cyclohexyl silanol, trimethyl cyclohexyl silanol and trimethyl cycloheptyl silanol, triphenyl silanol, tribenzyl silanol, triphenethyl silanol, and triphenpropyl silanol, diheptyl silanediol, diisoheptyl silanediol, dioctyl silanediol, diisooctyl silanediol, di-2-ethylhexyl silanediol, di-sec-octyl silanediol, di-tert-octyl silanediol, dinonyl silanediol, diisononyl silanediol, didecyl silanediol, dicyclopropyl silanediol, dicyclobutyl silanediol, dicyclopentyl silanediol, dicyclohexyl silanediol, dicycloheptyl silanediol, dicyclooctyl silanediol, dipropyl cyclohexyl silanediol, dimethyl cyclohexyl silanediol and dimethyl cycloheptyl silanediol; diphenyl silanediol, dibenzyl silanediol, diphenethyl silanediol, diphenpropyl silanediol; heptyl silanetriol, isoheptyl silanetriol, octyl silanetriol, isooctyl silanetriol, 2-ethylhexyl silanetriol, sec-octyl silanetriol, tert-octyl silanetriol, nonyl silanetriol, isononyl silanetriol, decyl silanetriol, cyclopropyl silanetriol, cyclobutyl silanetriol, cyclopentyl silanetriol, cyclohexyl silanetriol, cycloheptyl silanetriol, cyclooctyl silanetriol, propyl cyclohexyl silanetriol, methyl cyclohexyl silanetriol and methyl cycloheptyl silanetriol; phenyl silanetriol, benzyl silanetriol, phenethyl silanetriol, phenpropyl silanetriol, naphthyl silanetriol (where too unstable, the triols are used in the form of their ethers).

The final reaction product is the ceric hydrocarbyl silyloxide of the higher silanol, but it is believed that the lower silanol expedites the reaction by first forming a silyloxide with the cerium, this silyloxide being converted by transetherification with the higher silanol to the silyloxide of the higher silanol.

The above-described reactions can be carried out in the presence of an excess of the silanol, which also can be a solvent for the corresponding silyloxide. Inert solvents in addition to the reactant silanol may be needed in order to dissolve the ceric ammonium nitrate such as DME, or other glymers, THF or alcohols. Inert solvents also may be required to separate products from the nitrate by-products, for instance, pentane, benzene, toluene, pet. spirits etc. If desired, the solvent can be separated from the reaction product by distillation at atmospheric or reduced pressure, following completion of the reaction. It is understood that one or two molecules of a solvent such as DME for instance may remain coordinated to the cerium.

The reaction proceeds under anhydrous conditions at a temperature within the range from about $-30°$ C. to about $200°$ C., preferably from about $0°$ C. to about $50°$ C., most preferably at room temperature, depending on the solvent system and base used.

The case where ceric ammonium nitrate is totally or partially dissolved in an alcohol such as methanol, ethanol or isopropanol, or where the silanol is mixed with an alcohol and then added to the ceric ammonium nitrate is a special one that may involve going "in situ" via the alkoxide of cerium corresponding to the alcohol present. In some of these cases the reaction may take longer to complete and may require heating. In each, however, the product is the desired cerium silyloxide.

The reaction of the ceric ammonium nitrate proceeds in the presence of a suitable anhydrous base, such as ammonia, or an alkali metal reacted first with the silanol to produce the corresponding alkali metal silanolate which is then reacted with the ceric ammonium nitrate. A byproduct of the reaction is the corresponding ammonium or alkali metal nitrate salt.

The reaction time is not critical. The reaction is continued until the desired silyloxide product is formed. This may take from ten minutes to several hours, but it is not necessary to carry the reaction beyond a five hour reaction time. Usually, reaction is complete within from one to three hours.

The reaction can proceed quite rapidly at room temperature, and if it does, it very likely will also proceed at temperatures well below room temperature, down to $-30°$ C., but there is no reason to incur the additional expense of cooling the reaction mixture. The upper limit on reaction temperature is imposed by the volatility of the reaction mixture or any component thereof, and their decomposition temperature. There is no reason to use a temperature above the boiling point of the reaction mixture at atmospheric pressure, but if the boiling temperature is too low, as, for example, in the case of methanol, a closed reaction vessel or pressurized system can be used. The reaction temperature need not exceed $200°$ C., taking the above factors into consideration.

The amount of anhydrous base is stoichiometric, since the function of the base cation, ammonia or alkali metal, is to take up nitrate from the ceric ammonium nitrate starting material. An excess can be used, but is unnecessary.

The amount of silanol is at least from 1 to 6 moles per mole of ceric ammonium nitrate, but larger amounts can also be used. Larger than stoichiometric amounts will be used, of course, when the silanol is also to function as a solvent, according to the dilution of the reaction mixture required.

The reaction mixture contains the nitrate salt of the base cation, and this can be separated from the silyloxide during work-up. If this salt is less soluble in the reaction mixture than the silyloxide reaction product, it can be filtered off, and thereby separated from the reaction product. Alternatively, the reaction mixture can be taken up in an inert solvent such as benzene, DME, THF, toluene or hexane, preferably an inert solvent in which the silyloxide reaction product is soluble, and the nitrate or salt insoluble, whereupon the nitrate salt is filtered off or centrifuged out.

Depending on reaction and work-up conditions, the silyloxide can be isolated as associations with one or more molecules of alcohol or a solvent.

For some applications the cerium silyloxides can be used in the form in which they exist in the reaction mixture at the end of the reaction, without actually isolating them from the reaction mixture, or separating them from the nitrates, which saves processing and handling costs.

The following Examples in the opinion of the inventors represent preferred embodiments of the invention:

EXAMPLE 1

Preparation of cerium (IV) tetra(triphenyl silyloxide)

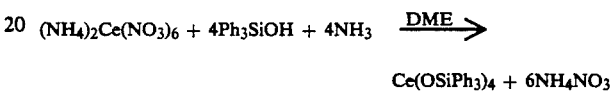

4 g (0.00729 m) of ceric ammonium nitrate was suspended in 40 ml (35 g) dimethoxy ethane. Upon adding 8 g (0.0291 m) of triphenylsilanol as a solid an almost clear orange solution was formed. In the next five minutes NH$_3$ gas was bubbled through the solution, causing an exothermic reaction (cooling was not necessary) along with immediate formation of a white precipitate. After stirring for an additional 10 minutes, the precipitate was isolated by using a frit filter. Subsequent evaporation of the obtained yellow filtrate to dryness resulted in an oily product, which however, became powdery upon further drying under vacuum (1 torr). The final product was a white powder, fairly air stable, yield: 8.5 g (94%).

Solubility: good in toluene; soluble in DME; moderately soluble in acetone; insoluble in n-hexane and acetone.

NMR results: $^1$H CHCl$_3$-d $\delta$3.15; 3.35; 7.06; 7.14; 7.18; 7.26; 7.53; 7.61. $^{13}$C CHCl$_3$-d $\delta$59.83; 71.79; 127.49; 129.17; 135.13; 137.57.

EXAMPLE 2

Preparation of cerium (IV) bis(1,1-diphenyl silyloxide)

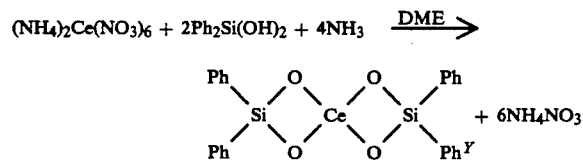

To a stirred suspension of 5 g (0.00912 mole) of (NH$_4$)$_2$Ce(NO$_3$)$_6$ in 40 ml (35 g) dimethoxy ethane, 3.94 g (0.0182 m) of Ph$_2$Si(OH)$_2$ was added as a solid, forming an almost clear red/orange solution. The bubbling of NH$_3$ gas through the solution caused an exothermic reaction, and the immediate formation of a white precipitate, while the (NH$_4$)$_2$Ce(NO$_3$)$_6$ was used up in a few minutes. After 10 minutes of stirring the reaction was regarded as complete, and subsequent filtration and removal of the solvent yielded 4.5 g (86%) of an orange/yellow powder.

Solubility: soluble in CH$_3$CN, DME, toluene, acetone; insoluble in n-hexane.

NMR results: $^1$H(THF-d$_8$) δ3.31; 3.48; 7.21; 7.66; 7.75. $^{13}$C(THF-d$_8$) δ58.84; 72.6; 128.02; 129.59; 135.33; 139.23.

EXAMPLE 3

Reaction of (NH$_4$)$_2$Ce(NO$_3$)$_6$ with 1Ph$_2$Si(OH)$_2$ (NH$_4$)$_2$Ce(NO$_3$)$_6$ + Ph$_2$Si(OH)$_2$ + 2NH$_3$ $\xrightarrow{DME}$

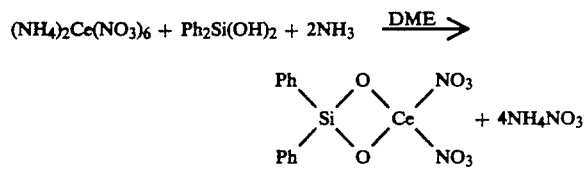

+ 4NH$_4$NO$_3$

Following the same procedure as in Example 2, to 5 g (0.00912 m) (NH$_4$)$_2$Ce(NO$_3$) in 40 ml (35 g) dimethoxy ethane 2 g Ph$_2$Si(OH)$_2$ (0.00924 m) was added as a solid. The reaction was complete after 10 minutes.

Yield: 3.5 g (85.2%) of an orange powder.

Solubility: soluble in CH$_3$CN, acetone, DME to form foggy solutions; insoluble in hexane and toluene.

$^1$H and $^{13}$C N-MR data are identical with those of Example 2.

EXAMPLE 4

Preparation of cerium (IV) tetra(triethyl silyloxide)

(NH$_4$)$_2$Ce(NO$_3$)$_6$ + 4ET$_3$SiOH + 4NH$_3$ $\xrightarrow{DME}$

Ce(OSiEt$_3$)$_4$ + 6NH$_4$NO$_3$

To the stirred suspension of 10.36 g (0.0189 mole) of (NH$_4$)$_2$Ce(NO$_3$)$_6$ in 50 ml (43 g) dimethoxy ethane, 10 g (0.0751 m) of triethyl silanol was added via a syringe. In the next ten minutes NH$_3$ gas was bubbled slowly through the orange/yellow solution, causing the immediate formation of a white precipitate. After stirring for additional 30 minutes, the mixture was filtered using a frit filter and the obtained yellow/green filtrate was evaporated to dryness. However, it was not possible to convert the obtained heavy yellow oil into a powder after several treatments under vacuum.

Yield of (NH$_4$)NO$_3$ recovered: 8.7 g (theory; according to the above reaction equation: 9 g)

NMR results: $^1$H(C$_6$H$_6$-d$_6$) δ0.62(t); 1.00 (q) $^{13}$C(C$_6$H$_6$-d$_6$) 6.94; 7.12. $^{29}$Si(C$_6$H$_6$-d$_6$) δ15.14.

EXAMPLE 5

Preparation of cerium (IV) bis(1,1-diphenyl silyloxide)

(NH$_4$)$_2$Ce(NO$_3$)$_6$ + 2Ph$_2$Si(OLi)$_2$ $\xrightarrow{DME}$

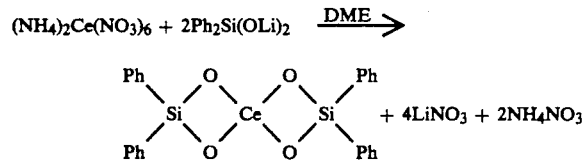

+ 4LiNO$_3$ + 2NH$_4$NO$_3$

To a stirred suspension of 3.4 g (0.02179 mole) of dilithiodiphenyldisilanolate in 30 ml (26 g) 5.97 g (0.0108 m) of DME (NH$_4$)$_2$Ce(NO$_3$)$_6$ was added as a solid. After 2 hrs of stirring a white precipitate and a dark red/brown solution had been formed. No unreacted (NH$_4$)$_2$Ce(NO$_3$)$_6$ was left. Subsequent evaporation of the solvent caused the formation of a dark red heavy oil. After keeping the oil for 10 hours at oil pump vacuum it was possible to convert it into a sticky, wet orange powder.

NMR results: $^1$H (CHCl$_3$-d) δ3.34; 3.51; 7.22; 7.30; 7.37; 7.52. $^{13}$C(CHCl$_3$-d) δ59.39; 71.74; 127.71; 130.04; 134.26.

EXAMPLE 6

Preparation of cerium (IV) tetra(trimethyl silyloxide)

(NH$_4$)$_2$Ce(NO$_3$)$_6$ + 6KOSiMe$_3$ $\xrightarrow{THF}$

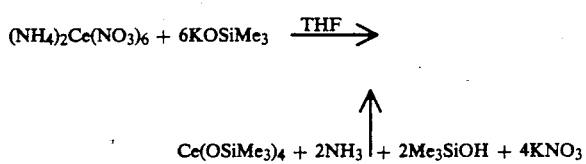

Ce(OSiMe$_3$)$_4$ + 2NH$_3$↑ + 2Me$_3$SiOH + 4KNO$_3$ 10.68 g (0.01948 m) (NH$_4$)$_2$Ce(NO$_3$)$_6$ and 15 g (0.1169 m) of potassium trimethyl silanolate were put together in a 200 ml flask. Upon adding of 40 ml of tetrahydrofuran, the mixture was stirred 8 hrs, after which time a greenish yellow precipitate had been formed. Upon filtration via a frit filter 45 ml of a clear colorless solvent mixture (THF+Me$_3$SiOH) and 16.5 g of a greenish/yellow powder [Ce(OSiMe$_3$)$_4$+NH$_4$NO$_3$] (theory: 17.5 g) was obtained. The powder was washed with 250 ml of distilled water in air, to yield 4.2 g of a light yellow powder ($\hat{=}$ 43%)

The product was a fairly air stable, in organic solvents insoluble fine powder. It is apparently not attacked by H$_2$O.

EXAMPLE 7

Preparation of cerium (IV) tetra(trimethyl siloxane)

(NH$_4$)$_2$Ce(NO$_3$)$_6$+6Me$_3$SiOH+NH$_3$.
→Ce(OSiMe$_3$)$_4$+6NH$_4$NO$_3$+2Me$_3$SiOH 10.2 g of ceric ammonium nitrate (0.0186 m) was suspended in 20 ml (17 g) of DME and stirred for 10 minutes. 12.3 ml ($\hat{=}$ 10.05 g $\hat{=}$ 0.1116 m) of trimethylsilanol were added via a syringe. As Me$_3$SiOH was not soluble in the red suspension of the cerium complex two layers have been formed. Under vigorous stirring NH$_3$ gas was bubbled through the solution accompanied by the formation of a bright yellow precipitate which turned to a pale yellow on further reaction with NH$_3$ gas. In the first 15 minutes the reaction proceeded very exothermically; however, after ½ hour the reaction temperature decreased. 40 ml of diethylether was added to maintain stirring.

Afterwards, the product was filtered and washed with 3×40 ml of ether. After drying at oil pump vacuum 12.1 g of a pale yellow powder was obtained. The product mixture containing NH$_4$NO$_3$ was washed 200 ml of H$_2$O. The remaining solid was dried at vacuum and 5.4 g of a light yellow powder was obtained (58.5%).

The product is not soluble in any common solvents.

EXAMPLE 8

Preparation of cerium (IV) tetra(triphenyl silyloxide)

(NH$_4$)$_2$Ce(NO$_3$)$_6$ + 6Ph$_3$SiONa $\xrightarrow{DME}$

Ce(OSiPh$_3$)$_4$ + 6NaNO$_3$ + 2NH$_3$ + 2Ph$_3$SiOH 3.9 g (0.013 m) of sodium triphenylsilanolate was dissolved in 30 ml of DME (26 g). This solution was dropped into the red clear solution of 1.19 g (0.00217 m) (NH$_4$)$_2$Ce(NO$_3$)$_6$ in 15 ml (13 g) of DME. A yellowish white precipitate was formed immediately along with NH$_3$ gas, as was indicated by pH paper. After stirring the mixture overnight the solvent was evaporated at 40° C. to yield 4.94 g (theory 5.0 g) of a light yellow powder. The crude product was washed with two portions of each 30 ml iso-propanol in order to remove Ph$_3$SiOH. The remaining residue was extracted with 45 ml of benzene to give a clear yellow filtrate. Upon removing the solvent in vacuum, 2.6 g (96%) of a white powder was obtained.

Soluble in CHCl$_3$, DME, THF, C$_6$H$_6$.

$^1$H and $^{13}$C NMR data are identical with those of Example 1.

EXAMPLE 9

Preparation of cerium (IV) tetra(triphenyl silyloxide)

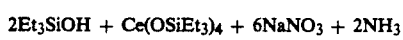

3.37 g (0.02173 m) of sodium triethylsilonate was prepared by reacting 0.5 g Na with 2.87 g Et$_3$SiOH in 30 ml (26 g) DME during 12 hours. To the clear colorless solution 1.98 g (0.0036 m) of (NH$_4$)$_2$Ce(NO$_3$)$_6$ (in 20 ml, 17 g DME) was added. A white precipitate was formed immediately along with NH$_3$ gas. After a reaction time of ~1 hour all of the (NH$_4$)$_2$Ce(NO$_3$)$_6$ had reacted. Following filtration the yellow filtrate was evaporated to dryness to yield a yellow oily product.

$^1$H and $^{13}$C NMR data are identical with those of Example 4.

EXAMPLE 10

Preparation of cerium (IV) bis(1,1-diphenyl silyloxide)

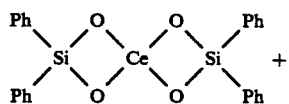

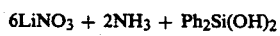

To the clear light yellow solution of 1.92 g (0.0084 m) Ph$_2$Si(OLi)$_2$ in 30 ml (24 g) methanol, was dropped the clear red solution of 1.53 g (NH$_4$)$_2$Ce(NO$_3$)$_6$ in 10 ml MeOH. A pale yellow precipitate was formed immediately along with NH$_3$ gas as was indicated by pH paper. After stirring for three hours the reaction mixture was filtered using a Schlenk frit; subsequent evaporation of the pale yellow filtrate to dryness yielded a pale yellow powder.

$^1$H and $^{13}$C NMR data are identical with those of Example 2, except that the product from methanol as solvent contains two coordinated MeOH molecules.

EXAMPLE 11

Preparation of cerium (IV) diisopropoxy-1,1-diphenylsilanediolate

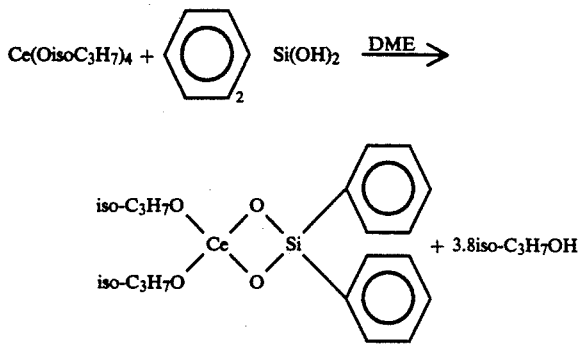

To the clear yellow solution of 6 g (0.01238 mole) Ce(OisoC$_3$H$_7$)$_4$ 1.8 isoC$_3$H$_7$OH in 30 ml (26 g) DME, 2.67 g (0.01238 m) of

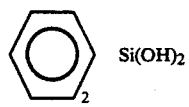

diphenylsilanediol was added as a solid. After a few minutes of stirring a thick suspension had been formed, by adding of ~10 ml of DME a clear solution was obtained, which was stirred for three hours. The solvent was removed with mild heating (~40° C.) under oil pump vacuum. Before complete drying the solid foamed up, but could be easily converted into a powder by using a spatula.

Yield: 5 g (85.5%) of a yellow, slightly air sensitive powder. Very soluble in CHCl$_3$, ether, DME, soluble in C$_6$H$_6$, not soluble in CH$_3$CN. m.p. 95°–100° C.

NMR results: $^1$H (CHCl$_3$-d) δ1.26; 1.33; 5.1; 7.26; 7.72. $^{13}$C (CHCl$_3$-d) δ27.75; 127.27; 128; 129; 134.85.

Elemental analyses: Calcd for C$_{18}$H$_{24}$O$_4$SiCe 472.205

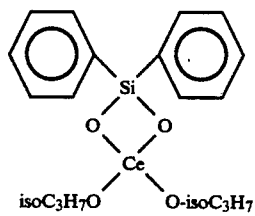

472.205 C 45.74(39.20); H 5.08(4.93) Si 5.94(6.04); Ce 29.64(30.60). Calcd for C$_{15}$H$_{26}$O$_5$SiCe: 454.205

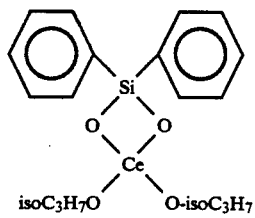

C 39.63; H 5.72; Si 6.18; Ce 30.84 in ( ) values found.

The yield of 85.5% has been based on the M.W. 472.205.

EXAMPLE 12

Preparation of cerium (IV) bis(iso-propoxide)-bis(trimethylsiloxane)

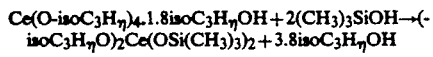

Ce(O-isoC$_3$H$_7$)$_4$.1.8isoC$_3$H$_7$OH + 2(CH$_3$)$_3$SiOH → (-isoC$_3$H$_7$O)$_2$Ce(OSi(CH$_3$)$_3$)$_2$ + 3.8isoC$_3$H$_7$OH 10.2 g (0.021 m) of ceric isopropoxide was dissolved in 20 ml (17 g) of DME. To the stirred solution 4.65 ml (≙ 3.79 g ≙ 0.042 m) of trimethylsilanol was added via a syringe. After each 30 minutes the red solution turned foggy and gradually a fine precipitate began to form. The mixture was allowed to react in the next four hours. Subsequent filtration via a Schlenk frit and drying at oil pump vacuum yielded 3.1 g of a pale yellow powder (33.8%).

NMR data: $^1$H(C$_6$H$_6$-d$_6$)δ0.3356; 1.34; 1.41; 4.30. $^{13}$C(C$_6$H$_6$-d$_6$)δ3.73; ,26.37; 71.98.

EXAMPLE 13

Preparation of cerium (IV) tetramethyl siloxydiolate-di-isopropoxide

Ce(O-isoC$_3$H$_7$)$_4$.1.0 isoC$_3$H$_7$OH +

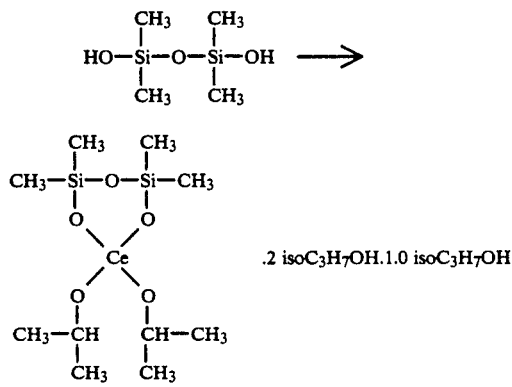

.2 isoC$_3$H$_7$OH.1.0 isoC$_3$H$_7$OH 13.74 g (0.0314 m) of ceric isopropoxide and 5.25 g (0.0314 m) of tetramethyl disiloxanol were dissolved in each 10 ml of DME. Upon adding the Si-compound to the Ce-complex solution a yellow precipitate was immediately formed which partially went into solution. However, by fast filtration and drying at vacuum, it was possible to recover Ca 100 mg of yellow precipitate.

NMR data: $^1$H(CHCl$_3$-d)δ0.0197; 1.26; 4.71. $^{13}$C(CHCl$_3$-d)δ0.9941; 27.05; 71.80.

After the filtration a clear red filtrate was obtained which on removing the solvent turned into a heavy oil. It was not possible to convert it into a powder by further drying. Its NMR data are almost identical with those of the above mentioned yellow precipitate.

The cerium hydrocarbyl silyloxides can be employed in the manufacture of oxide powders containing cerium and silicon, useful in preparing high performance ceramics; hard gels and films containing cerium and silicon; optical fibers containing cerium and silicon polymers or oxides; additives for biocides, additives for silicone coatings such as paints, treatment of textiles and other cellulosic materials. They can also be used in various catalytic applications as for instance curing of silicone rubber, and catalysts in the manufacture of polyurethane products. The Table illustrates the potentials of some of the new compounds in a standard test demonstrating and comparing catalytic activity:

| Compound Tested | Concentration ppm | Solidification Time min. |
|---|---|---|
| Nickel acetyl acetonate (a standard) | 314 | 115 |
| Ce(O$_2$SiPh$_2$)$_2$ | 260 | 105 |
| (PrO)$_2$Ce—(O$_2$SiPh$_2$) | 320 | 105 |
| (PrO)$_2$Ce—(OSiMe$_3$)$_2$ | 372 | 45 |
| Ce(OSiEt$_3$)$_4$ | 233 | 80 |
| Ce(OSiMe$_3$)$_4$ | 282 | 69 |

The reactions were run with polyoxypropylene triol (Union Carbide's NiAX Triol LG-56) and toluene diisocyanate in a procedure described in *Journal of Applied Polymer Science*, Vol IV, No. 1, pp 207–211 (1960).

Some of the new products are surprisingly resistant to hydrolysis, while others hydrolyze very slowly. Thus it is possible to form a silyloxide having any desired rate of hydrolysis, according to the application.

Furthermore, having silicon and cerium present together in the same molecule is advantageous when both are required, as compared to adding separate cerium and silicon alkoxides.

The term "ceric hydrocarbyl silyloxide" as used in this specification and in the claims generically encompasses any compound having cerium attached via oxygen to silicon of a silyloxide group, and also includes specifically such compounds containing, in addition nitrate groups and/or hydrocarbyloxy groups attached to cerium.

Having regard to the foregoing disclosure the following is claimed as inventive and patentable embodiments thereof:

1. A process for preparing ceric hydrocarbyl silyloxides which comprises reacting ceric ammonium nitrate with a hydrocarbyl silanol under anhydrous conditions in the presence of an anhydrous base at a temperature within the range from about −30° C. to about 200° C. until ceric hydrocarbyl silyloxide and the nitrate salt of the base are formed.

2. A process according to claim 1 in which the hydrocarbyl silanol is an aliphatic silanol in which the aliphatic groups have from one to six carbon atoms.

3. A process according to claim 1 in which the hydrocarbyl silanol is a hydrocarbyl silanol having hydrocarbyl groups selected from the group consisting of aliphatic, cycloaliphatic, aromatic and alkyl aromatic groups having from six to about ten carbon atoms.

4. A process according to claim 3 in which the hydrocarbyl silanol has the formula:

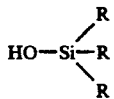

wherein:

R is hydrogen or a hydrocarbyl group having from one to about ten carbon atoms, and at least one R is a hydrocarbyl group.

5. A process according to claim 3 in which the hydrocarbyl silanol has the formula:

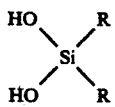

wherein:
R is hydrogen or a hydrocarbyl group having from one to about ten carbon atoms, and at least one R is a hydrocarbyl group.

6. A process according to claim 1 in which the hydrocarbyl silanol has the formula:

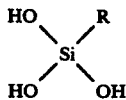

wherein:
R is a hydrocarbyl group having from one to about ten carbon atoms.

7. A process according to claim 6 in which the hydrocarbyl silanol is added in the form of the ether

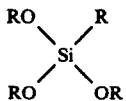

wherein:
R is a hydrocarbyl group having from one to about ten carbon atoms, and at least one R in OR is hydrogen.

8. A process according to claim 1 in which the hydrocarbyl silanol has the formula:

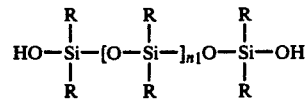

wherein:
R is hydrogen or a hydrocarbyl group having from one to about ten carbon atoms and at least one R is a hydrocarbyl group; and
$n_1$ is the number of such units and ranges from 1 to about 10.

9. A process according to claim 8 in which the hydrocarbyl silanol is a solid silicone resin containing free OH groups.

10. A process according to claim 1 carried out in solution in a solvent.

11. A process according to claim 10 carried out in the presence of an alcohol.

12. A process according to claim 11 in which the alcohol is an alkanol having from one to about ten carbon atoms.

13. A process according to claim 1 in which the amount of silanol is less than the stoichiometric amount to form the silyloxide.

14. A process according to claim 1, in which the amount of silanol is at least the stoichiometric amount to form the silyloxide.

15. A process according to claim 1 in which the anhydrous base is an alkali metal silyloxide of the silanol of the cerium hydrocarbyl silyloxide.

16. A process according to claim 1 carried out at a reaction temperature within the range from room temperature up to about 50° C.

17. A process according to claim 1, in which the cerium silyloxide reaction product is recovered and separated from the nitrate salt by extraction with a solvent for one of the silyloxide or the nitrate salt.

* * * * *